(12) United States Patent
Zhao et al.

(10) Patent No.: US 12,305,166 B2
(45) Date of Patent: May 20, 2025

(54) SEPARATION AND COLLECTION DEVICE FOR CELLS AND BIOMOLECULES, AND TESTING SYSTEM

(71) Applicant: BGI SHENZHEN, Shenzhen (CN)

(72) Inventors: Jing Zhao, Shenzhen (CN); Yuan Jiang, Shenzhen (CN); Wen-Wei Zhang, Shenzhen (CN); Xia Zhao, Shenzhen (CN); Ao Chen, Shenzhen (CN)

(73) Assignee: BGI SHENZHEN, Shenzhen (CN)

( * ) Notice: Subject to any disclaimer, the term of this patent is extended or adjusted under 35 U.S.C. 154(b) by 1138 days.

(21) Appl. No.: 17/267,452

(22) PCT Filed: Aug. 24, 2018

(86) PCT No.: PCT/CN2018/102346
§ 371 (c)(1),
(2) Date: Feb. 9, 2021

(87) PCT Pub. No.: WO2020/037684
PCT Pub. Date: Feb. 27, 2020

(65) Prior Publication Data
US 2021/0324373 A1 Oct. 21, 2021

(51) Int. Cl.
*C12N 15/10* (2006.01)
*B01L 3/00* (2006.01)
(Continued)

(52) U.S. Cl.
CPC .... *C12N 15/1013* (2013.01); *B01L 3/502715* (2013.01); *B01L 3/502753* (2013.01);
(Continued)

(58) Field of Classification Search
CPC .......... C12N 15/1013; B01L 3/502715; B01L 3/502753; B01L 3/502761; B01L 2300/0832; B01L 2400/043; B01L 2200/022; B01L 2200/025; B01L 2200/026; B01L 2200/0652; B01L 2200/0668;
(Continued)

(56) References Cited

U.S. PATENT DOCUMENTS

2017/0082625 A1* 3/2017 Agarwal ................ G01N 1/405
2017/0191914 A1 7/2017 Liu et al.
(Continued)

FOREIGN PATENT DOCUMENTS

CN 102690786 A * 9/2012 ............ C12M 25/16
CN 104560950 A 4/2015
(Continued)

*Primary Examiner* — John McGuirk
(74) *Attorney, Agent, or Firm* — ScienBiziP, P.C.

(57) ABSTRACT

A separation and collection device for cells and biomolecules includes an annular tube and several magnetic beads configured to identify and bind with different cells or molecules in the biological sample. The annular tube defines a through hole for the biological sample to exit. Sizes of different groups of magnetic beads are different. An aperture size of a through hole is changeable such that the plurality of groups of magnetic beads can flow through the through hole in a certain order. A testing system including the separation and collection device is further disclosed.

17 Claims, 3 Drawing Sheets

(51) Int. Cl.
*B03C 1/01* (2006.01)
*B03C 1/30* (2006.01)
*G01N 1/10* (2006.01)
*G01N 1/40* (2006.01)
*G01N 33/543* (2006.01)

(52) U.S. Cl.
CPC .......... *B01L 3/502761* (2013.01); *B03C 1/01* (2013.01); *B03C 1/30* (2013.01); *G01N 1/10* (2013.01); *G01N 1/4077* (2013.01); *G01N 33/54326* (2013.01); *B01L 2300/0832* (2013.01); *B01L 2400/043* (2013.01); *B03C 2201/18* (2013.01); *B03C 2201/22* (2013.01); *B03C 2201/26* (2013.01)

(58) Field of Classification Search
CPC ............. B01L 3/502; B01L 2300/0858; B01L 2400/0644; B03C 1/01; B03C 1/30; B03C 2201/18; B03C 2201/22; B03C 2201/26; B03C 1/286; G01N 1/10; G01N 1/4077; G01N 33/54326; C12M 1/00; C12M 1/24
See application file for complete search history.

(56) References Cited

U.S. PATENT DOCUMENTS

2017/0268037 A1* 9/2017 Ionescu-Zanetti .... B03C 1/0332
2017/0307488 A1 10/2017 Sarkar et al.

FOREIGN PATENT DOCUMENTS

CN 105219641 A 1/2016
WO WO-2013154345 A1 * 10/2013 ............. B01D 29/56

* cited by examiner

SEPARATION AND COLLECTION DEVICE FOR CELLS AND BIOMOLECULES, AND TESTING SYSTEM

FIELD

The subject matter relates to biotechnology, and more particularly, to a separation and collection device for cells and biomolecules, and a testing system using the device.

BACKGROUND

Blood is composed of plasma, white blood cells, platelets, and red blood cells, blood samples being the most accessible and minimally traumatic biopsy samples in clinical diagnosis. For cancer patients, white blood cells may be mixed with CTCs (circulating tumor cells) and CTM (circulating tumor microemboli), and their plasma may contain free ctDNA (circulating tumor DNA). The genetic information of ctDNA, CTC and CTM is required for tumor diagnosis, postoperative recurrence and metastasis, postoperative monitoring, efficacy evaluation, and drug resistance detection. The white blood cells also include T cells and B cells, which are of great significance for studying autoimmune diseases and inflammation. Finally, from the remaining white blood cells and platelets, gDNA (genomic DNA), mRNA (messenger RNA), and miRNA (microRNA) can be obtained by lysing the cells, so as to have a comprehensive genetic understanding of the blood. Blood sample collection and separation kits generally separate samples one by one, and it is difficult to separate multiple samples at the same time.

SUMMARY

Thus, a separation and collection device which can separate and collect multiple samples of cells and biomolecules at the same time, and a testing system including the device are needed.

The present disclosure provides a separation and collection device, for cells and biomolecules, including a first separation device. The first separation device includes an annular tube and a plurality of groups of magnetic beads. The annular tube is configured for containing a biological sample solution and defines a through hole for the biological sample solution to flow out. The groups of magnetic beads are configured to identify and bind with different cells or molecules in the biological sample. A size of each of the plurality of groups of magnetic beads is different. An aperture size of through hole is changeable such that the groups of magnetic beads can flow through the through hole in a certain order.

Furthermore, the annular tube includes an inner tube and an outer tube sleeved on the inner tube, a first bead hole is defined on the periphery wall of the inner tube, and a second bead hole is defined on a periphery wall of the outer tube. The second bead hole corresponds in position to the first bead hole, the second bead hole communicates with the first bead hole to form the through hole.

Furthermore, the first separation device further includes a first driving member, the outer tube and the inner tube are rotatable relative to each other, the driving member is connected to one of the inner tube and the outer tube and is configured to drive one of the inner tube and the outer tube to rotate relative to the other to change a overlapping area of the second bead hole and the first bead hole, thus changing the aperture size of the through hole.

Furthermore, the first separation device further includes a controller, the controller is connected to the first driving member and is configured to control the first driving member to drive the outer tube or the inner tube to rotate.

Furthermore, the annular tube further includes a pipe, an outlet is defined on a bottom of the outer tube, and the pipe communicates with the outlet.

Furthermore, the first separation device further includes a magnetic field generator which is configured to stir the biological sample solution in the annular tube, a magnetic field generated by the magnetic field generator acts on the inside of the inner tube. Furthermore, the first separation device further includes a second driving member, the second driving member is connected to the magnetic field generator and is configured to drive the magnetic field to move into or out of the annular tube. Furthermore, the plurality of groups of magnetic beads include a first group of magnetic beads for identifying and binding with ct/cfDNA in the biological sample, a second group of magnetic beads for identifying and binding with B cells in the biological sample, a third group of magnetic beads for identifying and binding with T cells in the biological sample, a fourth group of magnetic beads for identifying and binding with gDNA in the biological sample, and a fifth group of magnetic beads for identifying and binding with mRNA in the biological sample. Furthermore, after the first group of magnetic beads binds with ct/cfDNA, the second group of magnetic beads binds with B cells, and the third group of magnetic beads binds with T cells, the second driving member drives the magnetic field generator to move into the inner tube. After the first, second, and third groups of magnetic beads are adsorbed on the magnetic field generator, the second driving member drives the magnetic field generator to move out of the inner tube. After the fourth group of magnetic beads binds with gDNA, the fifth group of magnetic beads binds with mRNA, and the sixth group of magnetic beads binds with miRNA, the first group of magnetic beads bound with ct/cfDNA, the second group of magnetic beads bound with B cells, and the third group of magnetic beads bound with T cells are injected into the biological sample solution. Furthermore, the magnetic field generated by the magnetic field generator is an electromagnetic field, the second driving member can drive the magnetic field generator to enter the inner tube again, so removing the electromagnetic field generated by the magnetic field generator, after the fourth group of magnetic beads is bound with gDNA, after the fifth group of magnetic beads is bound with mRNA, and after the sixth group of magnetic beads is bound with miRNA. And then the electromagnetic field generated by the magnetic field generator is removed, such that the first group of magnetic beads bound with ct/cfDNA, the second group of magnetic beads bound with B cells, and the third group of magnetic beads bound with T cells, previously absorbed on the magnetic field generator, are released into the annular tube.

Furthermore, the separation and collection device further includes a collection device for collecting the first, second, third, fourth, fifth, and sixth groups of magnetic beads flowing out of the annular tube.

Furthermore, the collection device includes a plurality of channels, the annular tube defines a plurality of through holes, and the plurality of channels respectively communicate with the plurality of through holes.

Furthermore, the separation and collection device further includes a second separation device for separating CTCs and CTMs from the biological sample. Furthermore, the second separation device is a filter membrane.

A testing system includes a separation and collection device as above, a microfluidic system, and a gene sequencing system. The microfluidic system is combined with the separation and collection device. The gene sequencing system is combined with the microfluidic system.

In the separation and collection device, magnetic beads with different sizes can bind to cells or biomolecules with different sizes, and the magnetic beads of different sizes can pass through the through hole individually in a certain order, thereby simultaneously separating out various cells and biomolecules in the biological sample. The testing system of the present disclosure automates gene sequencing and improves processing efficiency.

SYMBOL DESCRIPTION OF MAIN COMPONENTS

Figure 1:
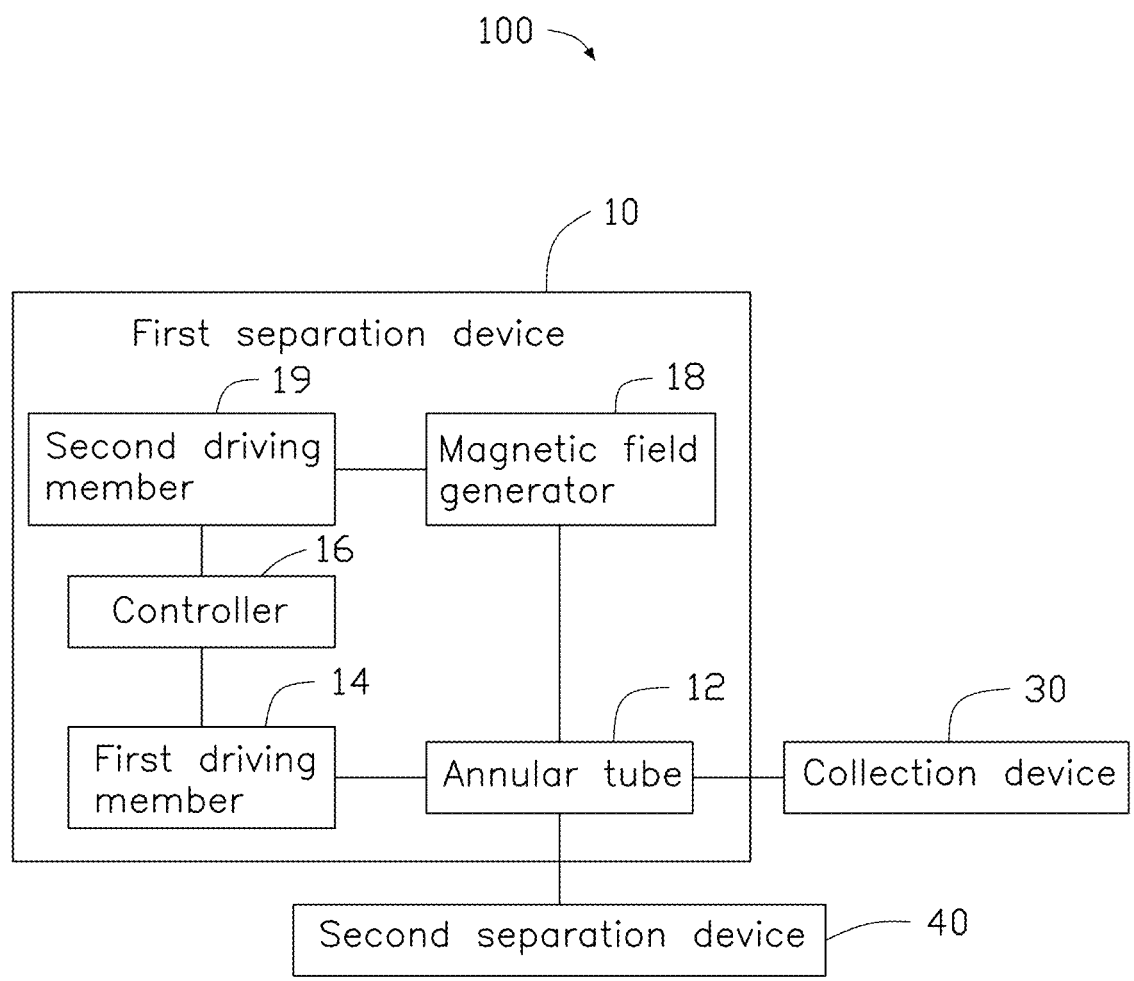
FIG. 1 is a block diagram of a separation and collection device of the present disclosure.

Separation and collection device 100
First separation device 10
Annular tube 12
Inlet 121
Through hole 124
Inner tube 122
Outer tube 123
First bead hole 125
Second bead hole 126
First driving member 14
Controller 16
Pipe 128
Magnetic field generator 18
Second driving member 19
Collection device 30
Second separation device 40
Testing system 200
Microfluidic system 210
Gene sequencing system 230

Implementations of the present technology will now be described, by way of example only, with reference to the attached figures.

DETAILED DESCRIPTION

In order to be able to understand the object, features, and advantages of the embodiments of the present disclosure, implementations of the disclosure will now be described, by way of embodiments only, with reference to the drawings. It should be noted that non-conflicting details and features in the embodiments of the present disclosure may be combined with each other.

In the following description, specific details are explained in order to make the embodiments of the present disclosure understandable. The described embodiments are only a portion of, rather than all of, the possible embodiments of the present disclosure. Based on the embodiments of the present disclosure, other embodiments obtained by a person of ordinary skill in the art without creative work shall be within the scope of the present disclosure.

It is noted that, when a first component is referred to as "connecting" to a second component, it is intended that the first component may be directly connected to the second component or may be indirectly connected to the second component via a third component between them. When a first component is referred to as "disposed" to a second component, it is intended that the first component may be directly disposed on the second component or may be indirectly disposed on the second component via a third component between them.

FIG. 1 is a block diagram of a separation and collection device 100 of an embodiment of the present disclosure. The separation and collection device 100 separates out and collects various cells, such as B cells and T cells, and various nucleic acid molecules, such as ct/cfDNA, gDNA, mDNA, and miRNA, in a biological sample. In the embodiment, the biological sample is a blood sample. It is to be understood that the biological sample can also be a sample obtained from other animals, plants, tissues, and cells, etc.

The separation and collection device 100 includes a first separation device 10, which is configured for separating out ct/cfDNA, B cells, T cells, ctDNA, gDNA, mDNA, and miRNA in the biological sample. The first separation device 10 performs a separation based on immunomagnetic separation technology. The first separation device 10 includes an annular tube 12 and a plurality of groups of magnetic beads.

Figure 2:
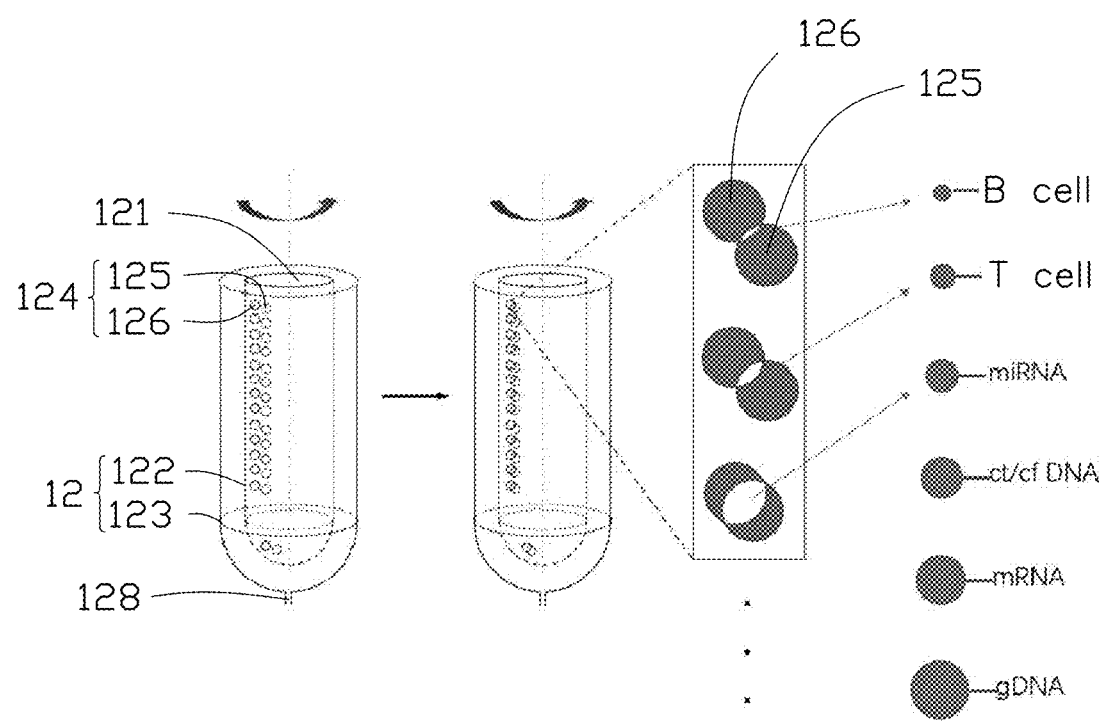
FIG. 2 is a schematic structural view of an annual tube of the device of FIG. 1.

FIG. 2 is a schematic structural view of the annular tube 12 of device 10 of FIG. 1. The annular tube 12 is configured for containing the biological sample. The annular tube 12 includes an inlet 121 at an end through which the biological sample solution can flow into the annular tube 12. The annular tube 12 defines a plurality of through holes 124 out of which the biological sample solution in the annular tube 12 can flow. In one embodiment, the through holes 124 are defined on the peripheral wall of the annular tube 12.

The plurality of groups of magnetic beads are configured to identify and bind with different cells or molecules in the biological sample. Size of each group of magnetic beads is different, and the groups of magnetic beads can each bind with cells or molecules with different sizes and flow out from differently-sized through holes 124. Specifically, the groups of magnetic beads include first to sixth groups of magnetic beads. The first group of magnetic beads is configured to identify and bind with ct/cfDNA in the biological sample. The second group of magnetic beads is configured to identify and bind with B cells in the biological sample. The third group of magnetic beads is configured to identify and bind with T cells in the biological sample. The fourth group of magnetic beads is configured to identify and bind with gDNA in the biological sample. The fifth group of magnetic beads is configured to identify and bind with mRNA in the biological sample. The sixth group of magnetic beads is configured to identify and bind with miRNA in the biological sample. When the first to sixth groups of magnetic beads are placed in the biological sample solution, they will respectively combine with ct/cfDNA, B cells. T cells, gDNA, mDNA, and miRNA in the biological sample, and flow out of the annular tube 12 through a certain through hole 124 with a certain size of aperture, so that the ct/cfDNA B cells, T cells, gDNA, mDNA and miRNA in the biological sample are separated.

It is to be understood, each group of the magnetic beads may include different sizes of magnetic beads. Each magnetic bead, of any size, includes magnetic nanoparticles with chemical surface treatment, and specific molecules binding to the surface of the magnetic nanoparticles. The chemical surface treatment is carried out on the surface of the magnetic nanoparticles such that functional groups with biochemical activities such as aldehyde, carboxyl, amino, or the like are formed on the surface of the magnetic nanoparticles. These functional groups render specific biocompatibility to the treated magnetic nanoparticles, so that a corresponding antigen, antibody, or nucleic acid will be recognized and will be bound by coupling with the ligand in the biologically active substance. The material of the magnetic nanoparticles is ferromagnetic material or paramagnetic material. The paramagnetic material includes aluminum, magnesium, platinum, or other materials that are weakly attracted by magnets. The ferromagnetic material includes nickel, cobalt, pure iron, iron alloys, or other materials that are strongly attracted by magnets. The specific molecules are molecules capable of binding with ct/cfDNA, B cell, T cell, gDNA, mDNA, or miRNA. In the embodiment, the specific molecules for binding with B cells and T cells are immune antibodies, and the specific molecules for binding with ct/cfDNA, gDNA, mDNA, and miRNA are oligos.

The annular tube 12 includes an inner tube 122 and an outer tube 123 sleeved on the inner tube 122. The inner tube 122 and the outer tube 123 are substantially cylindrical. The inner tube 122 and the outer tube 123 may be spherical or have any other shape. The inner tube 122 and the outer tube 123 are respectively provided with openings at the same end, and the opening of the inner tube 122 is substantially flush with the opening of the outer tube 123. The inner tube 122 is inserted into the outer tube 123 through the opening of the outer tube 123 and is received in the outer tube 123. The opening of the inner tube 122 serves as the inlet 121 of the annular tube 12. First bead holes 125 are defined on a periphery wall of the inner tube 122. Second bead holes 126 are defined on the periphery wall of the outer tube 123. The second bead holes 126 correspond in position to the first bead holes 125, and the communicating part of each second bead hole 126 and a corresponding first bead hole 125 form the through hole 124. Specifically, the overlapping portions of each of the second bead holes 126 and one of the first bead holes 125 together form the through hole 124. In the embodiment, the sizes of the second bead holes 126 are substantially the same as the sizes of the first bead holes 125.

The outer tube 123 and the inner tube 122 can rotate relative to each other. The first separation device 10 further includes a first driving member 14. The driving member 14 is connected to one of the inner tube 122 and the outer tube 123, and is configured to drive one of the inner tube 122 and the outer tube 123 to rotate relative to the other to change a overlapping area of each second bead hole 126 and one first bead hole 125. The aperture size of each through hole 124 is thereby changed. The aperture size of each through hole 124 corresponds with a size of each bead of the respective first to fourth groups of magnetic beads. It is to be noted, the aperture size of each of the through holes 124 corresponding to the size of the magnetic beads means that the aperture size of each of the through holes 124 is approximately the same as the size of one of the magnetic beads bound with the corresponding cells or molecules, or that while the aperture size of each of the through holes 124 is larger than the size of one of the magnetic beads, it is smaller than the size of magnetic beads bound with other cells or molecules. Specifically, the outer tube 123 is rotatably sleeved on the inner tube 122, the first driving member 14 is connected to the outer tube 123 for driving the outer tube 123 to rotate relative to the inner tube 122. It is to be understood, in other embodiments, the inner tube 122 may be rotatably disposed in the outer tube 123, the first driving member 14 can be connected to the inner tube 122 for driving the inner tube 122 to rotate relative to the outer tube 123.

When the ct/cfDNA needs to be separated out, the first driving member 14 drives the outer tube 123 to rotate to change the overlapping area of one of the second bead holes 126 and the corresponding one of the first bead holes 125, so that the aperture size of one of the through holes 124 is matched with the size of the first group of magnetic beads bound with the ct/cfDNA. Only the first group of magnetic beads bound with the ct/cfDNA can flow out from the through holes 124, thereby separating out the first group of magnetic beads bound with the ct/cfDNA. Similarly, when the B cells need to be separated out, the first driving member 14 drives the outer tube 123 to rotate to change the aperture size of each of the through holes 124 so that only the second group of magnetic beads bound with the B cells can flow out from the through holes 124. When the T cells need to be separated out, the first driving member 14 drives the outer tube 123 to rotate to change the aperture size of each of the through holes 124, so that only the third group of magnetic beads bound with the T cells can flow out from the through holes 124. When the gDNA needs to be separated out, the first driving member 14 drives the outer tube 123 to rotate to change the aperture size of each of the through holes 124, so that only the fourth group of magnetic beads bound with the gDNA can flow out from the through holes 124. When the mRNA needs to be separated out, the first driving member 14 drives the outer tube 123 to rotate to change the aperture size of each of the through holes 124, so that only the fifth group of magnetic beads bound with the mRNA can flow out from the through holes 124. When the miRNA needs to be separated out, the first driving member 14 drives the outer tube 123 to rotate to change the aperture size of each of the through holes 124, so that only the sixth group of magnetic beads bound with the miRNA can flow out from the through holes 124. It is to be understood, in order to enable the magnetic beads respectively bound with ct/cfDNA, B cells, T cells, gDNA, mDNA, or miRNA to flow out from the through holes 124 in the order of smaller to larger, the B cells, T cells, miRNA, ct/cfDNA, mRNA, and gDNA can be separated in that order.

It is to be understood, in other embodiments, a plurality of through holes 124 with different apertures can be directly defined on the sleeve 12, and the opening and closing of the through holes 124 can be controlled. For example, a plurality of cover plates can cover the through holes 124, the opening or closing of through holes 124 is controlled by opening or closing the cover plates. The aperture sizes of the through holes 124 are respectively matched with the sizes of the magnetic beads bound with ct/cfDNA, B cells, T cells, gDNA, mDNA, or miRNA, and by controlling the opening and closing of the through holes 124 with different aperture sizes, the magnetic beads bound with ct/cfDNA, B cells, T cells, gDNA, mRNA, or miRNA can flow out from the through holes 124 in the order of smaller to larger.

It is to be understood, in other embodiments, the number of the through holes 124 may be one or two, the number of the first bead holes 125 or the second bead holes 126 is the same as the number of the through holes 124.

The first separation device 10 further includes a controller 16. The controller 16 is connected to the driving member 14 and is configured to control the first driving member 14 to drive the outer tube 123 or the inner tube 122 to rotate, thereby controlling changing the aperture size of each of the through holes 124. The controller 16 further controls the frequency of the size-changing. The controller 16 controls the aperture size of each of the through holes 124 to change from smaller to larger, so that the magnetic beads with different sizes can flow out from each of the through holes 124 individually in the order of smaller to larger.

The annular tube 12 further includes a pipe 128. An outlet is defined on a bottom of the outer tube 123. The pipe 128 communicates with the outlet. The biological sample solution overflowing from the inner tube 122 into the gap between the outer tube 123 and the inner tube 122 flows out of the annular tube 12 through the pipe 128.

The first separation device 10 further includes a magnetic field generator 18 for generating a magnetic field. The magnetic field generated by the magnetic field generator 18 acts on the inside of the inner tube 122, so that the magnetic beads are attracted and adsorbed on the magnetic field generator 18. The magnetic field generator 18 is further configured to stir the biological sample solution, so that the magnetic beads can flow out from the through holes 124 smoothly. In the embodiment, the magnetic field generated by the magnetic field generator 18 is an electromagnetic field, for example, the magnetic field generator 18 is an electromagnetic rod. It is to be understood, in other embodiments, the magnetic field generated by the magnetic field generator 18 may be a constant magnetic field, for example, the magnetic field generator 18 can be a rubidium ferromagnetic rod.

The first separation device 10 further includes a second driving member 19. The second driving member 19 is connected to the magnetic field generator 18 and is configured for driving the magnetic field generator 18 to move into or out of the inner tube 122 and for driving the magnetic field generator 18 to stir the biological sample solution. The second driving member 19 is further connected to the controller 16, the controller 16 controls the second driving member 19 to drive the magnetic field generator 18.

In use, the first to third groups of magnetic beads are injected into the biological sample solution. After the first group of magnetic beads binds with ct/cfDNA, the second group of magnetic beads binds with B cells, and the third group of magnetic beads binds with T cells, the second driving member 19 drives the magnetic field generator 18 to move into the inner tube 122. The first to third groups of magnetic beads are attracted and adsorbed on the magnetic field generator 18 under the action of the magnetic field. Then the second driving member 19 drives the magnetic field generator 18 to move out of the inner tube 122. Then the fourth to sixth groups of magnetic beads are injected into the biological sample solution. After the fourth group of magnetic beads binds with gDNA, the fifth group of magnetic beads binds with mRNA, and the sixth group of magnetic beads binds with miRNA, the first group of magnetic beads bound with ct/cfDNA, the second group of magnetic beads bound with B cells, and the third group of magnetic beads bound with T cells are injected into the biological sample solution. When the magnetic field venerated by the magnetic field generator 18 is an electromagnetic field, after the fourth group of magnetic beads binds with gDNA, the fifth group of magnetic beads binds with mRNA, and the sixth group of magnetic beads binds with miRNA, the second driving member 19 drives the magnetic field generator 18 to enter the inner tube 122 again, and the electromagnetic field generated by the magnetic field generator 18 is removed. Thus the first group of magnetic beads bound with ct/cfDNA, the second group of magnetic beads bound with B cells, and the third group of magnetic beads bound with T cells, previously absorbed on the magnetic field generator 18 are released into the biological sample solution. When the magnetic field generated by the magnetic field generator 18 is a constant magnetic field, after the second driving member 19 drives the magnetic field generator 18 to move out of the inner tube 122, the first group of magnetic beads bound with ct/cfDNA, the second group of magnetic beads bound with B cells, and the third group of magnetic beads bound with T cells are separated from the magnetic field generator 18 under the action of an external force. Then after the fourth group of magnetic beads bind with gDNA, the fifth group of magnetic beads bind with mRNA, and the sixth group of magnetic beads bind with miRNA, the first group of magnetic beads bound with ct/cfDNA, the second group of magnetic beads bound with B cells, and the third group of magnetic beads bound with T cells are directly injected into the biological sample solution.

The separation and collection device further includes a collection device 30 for collecting the first to sixth groups of magnetic beads flowing out of and exiting the annular tube 12. Specifically, the collection device 30 includes a plurality of channels which are respectively communicate with the plurality of through holes 124, so as to collect the magnetic beads flowing out of the through holes 124 one by one. It is to be understood, the collection device 30 can include only one channel, and the magnetic beads flowing out through the plurality of through holes 124 are collected in the collection device 30 through the single channel.

The separation and collection device 100 further includes a second separation device 40 for separating CTCs and CTMs from the biological sample. The second separation device 40 separates the CTCs and CTMs by size of epithelial tumor cells. Specifically, the second separation device 40 is a filter membrane, which is housed in the inner tube 122 of the annular tube 12 and divides the inner cavity of the inner tube 122 into upper and lower parts for filtering CTCs and CTM in the biological sample solution. After filtering out CTCs and CTM, the ct/cfDNA, B cells, T cells, ctDNA, gDNA, mDNA and miRNA in the biological sample solution are separated. It is to be understood, in other embodiments, the filter membrane may be arranged above or at the inlet of the annular tube 12. The filter membrane can be any membrane that can be used for filtering, such as polycarbonate (Track-etched) membrane, micro sieve membrane, micro grid membrane, etc. In the embodiment, the pore size of the filter membrane is about 2.6 to 10 micrometers. CTCs are cells with a size greater than 25 micrometers, with a high ratio of nuclear to cytoplasmic cells, and which may have abnormal chromosomes and nuclei. CTM is a group of tumor cells bound together thus that CTM has a large size. After being filtered by the filter membrane, CTCs and CTMs with larger sizes are caught on the filter membrane, thereby enabling separation of CTCs and CTM. The separated CTCs and CTM can be taken out for identification by staining.

In an alternative embodiment, the second separation device 40 is a filter. The second separation device 40 communicates with the first separation device 10. After CTCs and CTMs in the biological sample are separated by the second separation device 40, the biological sample solution is injected into the first separation device 10 to separate ct/cfDNA, B cells, T cells, ctDNA, gDNA, rDNA, and miRNA. The second separation device 40 includes a bottle and a filter membrane. The filter membrane is placed in the filter bottle, and the inner cavity of the filter bottle is divided into upper and lower parts for filtering CTCs and CTM in the biological sample solution. After the red blood cells in the blood sample are lysed, they are injected into the bottle, filtered through the filter membrane, and then flow down to the bottom of the bottle. It is to be understood, the bottle can be integrally formed or assembled from components.

The second separation device 40 further includes a pressure detection device and a pressure pump. The pressure pump communicates with the part of the bottle below the filter membrane and is used to adjust the pressure of the cavity below the filter membrane in the bottle. Such adjustment changes a filtration rate of the biological sample passing through the filter membrane. The pressure detection device is used to detect the pressure of the cavity below the filter membrane in the bottle. The pressure pump automatically adjusts the pressure of the cavity below the filter membrane in the filter bottle according to the pressure that is detected by the pressure detection device.

It is to be understood, in other embodiment, the second separation device 40 can perform separation of the CTCs by using a surface-functionalized membrane or a surface-functionalized pipeline. EpCAM (epithelial cell adhesion molecule) and cytokeratin's 4-6, 8, 10, 13 or 19 are highly expressed in CTCs. Anti-EpCAM antibody and anti-cytokeratin's 4-6, 8, 10, 13 or 19 antibody are coupled to the surfaces of membrane or pipeline. When the biological sample flows over the surface of the membrane or through the pipeline, the surface antigen of CTCs can be combined with the corresponding antibody, thereby capturing CTCs. Since CD45 is not expressed in CTCs, CTCs can be isolated by negative selective of CD45. It is to be understood, in other embodiments, the second separation device 40 can also separate CTCs using the principles of Dean vortices.

In the separation and collection device 100, the magnetic beads with different sizes can bind with cells or biomolecules with different sizes. The first driving member 14 can drive the outer tube 123 to rotate to adjust the aperture size of each of the through holes 124, so that the magnetic beads of different sizes can pass through one of the through holes 124 individually in a certain order, thereby separating various cells and biomolecules in the biological sample as steps in a single process.

Figure 3:
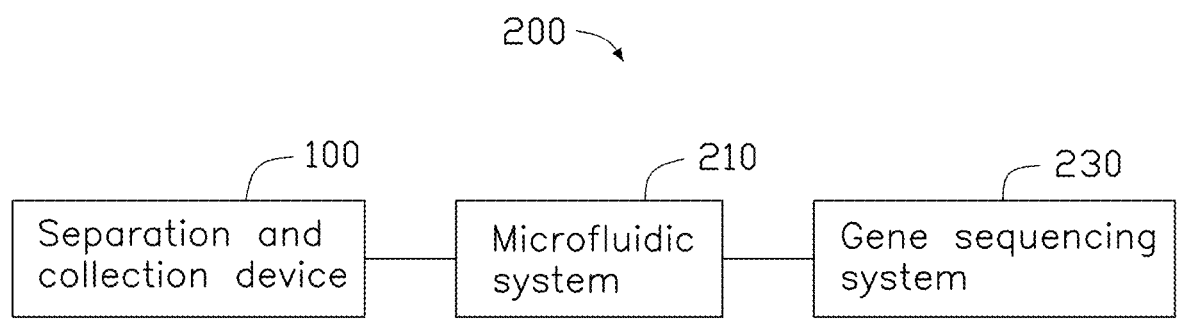
FIG. 3 is a block diagram of a testing system of the present disclosure.

FIG. 3 is block diagram of a testing system 200 of the present disclosure. The testing system 200 includes the separation and collection device 100, a microfluidic system 210, and a gene sequencing system 230. The microfluidic system 210 is combined with the separation and collection device 100 and is configured to construct a sequencing library with nucleic acid molecules which have been separated out by the separation and collection device 100. The gene sequencing system 230 is combined with the microfluidic system 210 and is configured to perform base sequence detection on different nucleic acid molecules which have been isolated. The testing system 200 automates gene sequencing and improves processing efficiency.

Even though information and advantages of the present embodiments have been set forth in the foregoing description, together with details of the structures and functions of the present embodiments, the disclosure is illustrative only. Changes may be made in detail, especially in matters of shape, size, and arrangement of parts within the principles of the present exemplary embodiments, to the full extent indicated by the plain meaning of the terms in which the appended claims are expressed.

What is claimed is:

1. A separation and collection device for cells and biomolecules, comprising:
a first separation device comprising:
an annular tube configured for containing a biological sample, the annular tube defining a through hole for the biological sample to flow out; and
a plurality of groups of magnetic beads configured to identify and bind with different cells or molecules in the biological sample, a size of each of the plurality of groups of magnetic beads being different;
wherein an aperture size of the through hole is changeable such that the plurality of groups of magnetic beads can flow through the through hole in a certain order; and
the annular tube comprises an inner tube and an outer tube sleeved on the inner tube, a first bead hole is defined on the periphery wall of the inner tube, and a second bead hole is defined on a periphery wall of the outer tube, the second bead hole corresponds in position to the first bead hole, the second bead hole communicates with the first bead hole to form the through hole, and the outer tube and the inner tube are rotatable relative to each other.

2. The separation and collection device of claim 1, wherein the first separation device further comprises a first driving member, and the first driving member is connected to one of the inner tube and the outer tube and is configured to drive one of the inner tube and the outer tube to rotate relative to the other to change an overlapping area of the second bead hole and the first bead hole, thus changing the aperture size of the through hole.

3. The separation and collection device of claim 2, wherein the first separation device further comprises a controller, and the controller is connected to the first driving member and is configured to control the first driving member to drive the outer tube or the inner tube to rotate.

4. The separation and collection device of claim 1, wherein the annular tube further comprises a pipe, an outlet is defined on a bottom of the outer tube, and the pipe communicates with the outlet.

5. The separation and collection device of claim 1, wherein the first separation device further comprises a magnetic field generator which is configured to stir the biological sample solution in the annular tube, and a magnetic field generated by the magnetic field generator acts on the inside of the inner tube.

6. The separation and collection device of claim 5, wherein the plurality of groups of magnetic beads comprises a first group of magnetic beads for identifying and binding with ct/cfDNA in the biological sample, a second group of magnetic beads for identifying and binding with B cells in the biological sample, a third group of magnetic beads for identifying and binding with T cells in the biological sample, a fourth group of magnetic beads for identifying and binding with gDNA in the biological sample, a fifth group of magnetic beads for identifying and binding with mRNA in the biological sample, and a sixth group of magnetic beads for identifying and binding with miRNA;
wherein after the first group of magnetic beads binds with ct/cfDNA, the second group of magnetic beads binds with B cells, and the third group of magnetic beads binds with T cells, a second driving member drives the magnetic field generator to move into the inner tube; after the first group of magnetic beads, the second group of magnetic beads, and the third group of magnetic beads are adsorbed on the magnetic field generator, the second driving member drives the magnetic field generator to move out of the inner tube; and after the fourth group of magnetic beads binds with gDNA, the fifth group of magnetic beads binds with mRNA, and the sixth group of magnetic beads binds with miRNA, the first group of magnetic beads bound with ct/cfDNA, the second group of magnetic beads bound with B cells, and the third group of magnetic beads bound with T cells are injected into the biological sample solution.

7. The separation and collection device of claim 6, further comprising a collection device for collecting the first group of magnetic beads, the second group of magnetic beads, the third group of magnetic beads, the fourth group of magnetic beads, the fifth group of magnetic beads, and the sixth group of magnetic beads flowing out of the annular tube.

8. The separation and collection device of claim 1, further comprising a second separation device for separating CTCs and CTMs from the biological sample, wherein the second separation device is a filter membrane.

9. The separation and collection device of claim 6, wherein the magnetic field generated by the magnetic field generator is an electromagnetic field, after the fourth group of magnetic beads binds with gDNA, the fifth group of magnetic beads binds with mRNA, and the sixth group of magnetic beads binds with miRNA, the second driving member drives the magnetic field generator to enter the inner tube again, and the electromagnetic field generated by the magnetic field generator is removed, such that the first group of magnetic beads bound with ct/cfDNA, the second group of magnetic beads bound with B cells, and the third group of magnetic beads bound with T cells, previously absorbed on the magnetic field generator are released into the annular tube.

10. The separation and collection device of claim 7, wherein the collection device comprises a plurality of channels, the annular tube defines a plurality of through holes, and the plurality of channels respectively communicate with the plurality of through holes.

11. A testing system comprising:
a separation and collection device for cells and biomolecules, comprising:
a first separation device comprising:
an annular tube configured for containing a biological sample, the annular tube defining a through hole for the biological sample to flow out, and
a plurality of groups of magnetic beads configured to identify and bind with different cells or molecules in the biological sample, a size of each of the plurality of groups of magnetic beads being different;
a microfluidic system combined with the separation and collection device; and
a gene sequencing system combined with the microfluidic system;
wherein an aperture size of the through hole is changeable such that the plurality of groups of magnetic beads can flow through the through hole in a certain order; and
the annular tube comprises an inner tube and an outer tube sleeved on the inner tube, a first bead hole is defined on the periphery wall of the inner tube, a second bead hole is defined on a periphery wall of the outer tube, the second bead hole corresponds in position to the first bead hole, the second bead hole communicates with the first bead hole to form the through hole, and the outer tube and the inner tube are rotatable relative to each other.

12. The testing system of claim 11, wherein the first separation device further comprises a first driving member, and the first driving member is connected to one of the inner tube and the outer tube and is configured to drive one of the inner tube and the outer tube to rotate relative to the other to change an overlapping area of the second bead hole and the first bead hole, thus changing the aperture size of the through hole.

13. The testing system of claim 12, wherein the first separation device further comprises a controller, and the controller is connected to the first driving member and is configured to control the first driving member to drive the outer tube or the inner tube to rotate.

14. The testing system of claim 11, wherein the annular tube further comprises a pipe, an outlet is defined on a bottom of the outer tube, and the pipe communicates with the outlet.

15. The testing system of claim 11, wherein the first separation device further comprises a magnetic field generator which is configured to stir the biological sample solution in the annular tube, and a magnetic field generated by the magnetic field generator acts on the inside of the inner tube.

16. The testing system of claim 15, wherein the first separation device further comprises a second driving member, and the second driving member is connected to the magnetic field generator and is configured to drive the magnetic field generator to move into or out of the annular tube.

17. The testing system of claim 11, wherein the separation and collection device further comprises a second separation device for separating CTCs and CTMs from the biological sample, wherein the second separation device is a filter membrane.

* * * * *